United States Patent [19]

Gries et al.

[11] 4,328,202

[45] May 4, 1982

[54] IONIC 5-C-SUBSTITUTED 2,4,6-TRIIODOISOPHTHALIC ACID DERIVATIVES

[75] Inventors: Heinz Gries; Heinrich Pfeiffer; Ulrich Speck; Wolfgang Muetzel, all of Berlin, Fed. Rep. of Germany

[73] Assignee: Schering, A.G., Berlin, Fed. Rep. of Germany

[21] Appl. No.: 223,634

[22] Filed: Jan. 9, 1981

[30] Foreign Application Priority Data

Jan. 11, 1980 [DE] Fed. Rep. of Germany ....... 3001293

[51] Int. Cl.³ .................. A61K 49/04; C07C 63/08; C07C 63/10
[52] U.S. Cl. .................................. 424/5; 562/442; 560/65; 562/37; 260/501.16; 260/501.11; 544/107; 430/967
[58] Field of Search ............... 562/449, 442; 424/5; 560/65, 37; 536/18; 260/501.16, 501.11; 544/107; 430/967

[56] References Cited

U.S. PATENT DOCUMENTS 3,622,616 11/1971 Gverbet et al. ............. 424/5 X
3,819,821 6/1974 Tilly ............................. 424/5
4,107,286 8/1978 Tilly et al. ................... 424/5

*Primary Examiner*—Bernard Helfin
*Attorney, Agent, or Firm*—Millen & White

[57] ABSTRACT

Ionic compounds of the formula

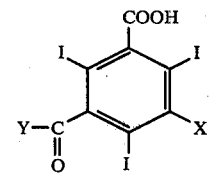

wherein X is $-CONR_1R_2$, $-CH_2NH\cdot Acyl$ or $-CH_2OH$; Y is $-NR_3R_4$, $-NH\cdot Acyl$ or $OR_5$; $R_1$, $R_2$, $R_3$ and $R_4$ can be identical or different, and each is hydrogen, $C_{1-6}$- alkyl or $C_{2-8}$-alkyl substituted by 1-5 OH groups and/or by one $C_{1-3}$-alkoxy group, $R_5$ is $C_{1-6}$ alkyl or $C_{2-8}$-alkyl substituted by 1-5 OH groups and/or by one $C_{1-3}$-alkoxy group, and Acyl, which can be the same or different in X and Y, is $C_{2-6}$-alkanoyl or $C_{2-6}$-alkanoyl substituted by 1-4 OH groups and/or by one $C_{1-3}$-alkoxy group, or a physiologically compatible salt thereof with an inorganic or organic base, have valuable properties as X-ray contrast agents.

22 Claims, No Drawings

IONIC 5-C-SUBSTITUTED 2,4,6-TRIIODOISOPHTHALIC ACID DERIVATIVES

CROSS REFERENCE TO RELATED APPLICATIONS

This application is related to commonly assigned U.S. application Ser. No. 223,619, filed on even date, and of common inventorship.

BACKGROUND OF THE INVENTION

Since the introduction of the triiodinated benzoic acid derivatives for use as opacifying substances in contrast media for the reproduction of blood vessels, the excretory urinary tract, and other body cavities and tissues in X-ray diagnostics, a large number of derivatives has been synthesized, tested and, in part, also utilized in practice.

Almost all of the heretofore described compounds are derived from the two basic structures of triiododiaminobenzoic acid and triiodoaminoisophthalic acid. The derivatives of both basic structures do not satisfy the ever increasing requirements which must be met by an ideal X-ray contrast medium. The most important properties are high contrast density, chemical stability, and maximally complete[100%] nontoxicity of the active agent, low viscosity of the liquid preparation, and pharmacodynamic properties adapted to the form of administration. The "ideal contrast medium" should combine all of these properties.

The relatively good compatibility of the presently conventional X-ray contrast media is attained by detoxifying the lipophilic and toxic basic structures by adding on strongly hydrophilic substituents. On the other hand, it is known that the possible variations of the two aforementioned basic structures are considerably restricted by the requirements to be met by an ideal contrast medium with respect to contrast density, stability, and viscosity, especially also in view of the fact that, for practical use, only compounds having a high iodine content are suitable.

Since the synthetic possibilities have been extensively exhausted in the meantime, the introduction of a novel basic structure would be of special value.

SUMMARY OF THE INVENTION

Therefore, it is an object of the present invention to provide such novel basic structures for use in X-ray contrast media, which structures, per se, furthermore, are maximally hydrophilic and nontoxic.

Upon further study of the specification and appended claims, further objects and advantages of this invention will become apparent to those skilled in the art.

These objects have been attained by providing novel ionic 2,4,6-triiodoisophthalic acid compounds, C-substituted in the 5-position, of Formula I

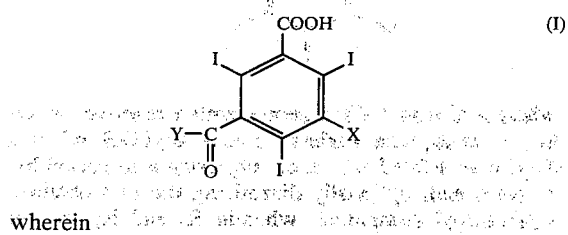

wherein

X is $-CONR_1R_2$, $-CH_2NH.Acyl$, or $-CH_2OH$;
Y is $-NR_3R_4$, $-NH.Acyl$, or $OR_5$,
$R_1$, $R_2$, $R_3$ and $R_4$ can be identical or different, and each is hydrogen or an optionally mono- or polyhydroxylated, straight-chain or branched lower alkyl group;
$R_5$ is an optionally mono- or polyhydroxylated, straight-chain or branched lower alkyl group, and
Acyl can be the same or different in X and Y, and is the acyl group of an optionally hydroxylated lower aliphatic carboxylic acid; in $R_1$, $R_2$, $R_3$, $R_4$, $R_5$ and Acyl any present OH-groups can also be etherified; and the salts thereof,
as well as a process for the preparation thereof, and novel X-ray contrast media containing compounds of Formula I as the opacifying substance.

DETAILED DISCUSSION

The unsubstituted alkyl groups $R_1$ through $R_5$, which can be straight-chain or branched, contain 1-6, preferably 1-4, especially 1-2 carbon atoms. Examples include, in particular, methyl, ethyl, and propyl; methyl is preferred.

If alkyl is a mono- or polyhydroxyalkyl residue, it also can be straight-chain or branched. Preferably suitable are alkyl residues of 2-8, preferably 2-4 carbon atoms. The hydroxy groups in the alkyl residue can be present as primary and/or secondary and/or tertiary hydroxy groups. The alkyl groups can contain 1-5, preferably 1-3 hydroxy groups. Examples include tris(hydroxymethyl)methyl, 1,3,4-trihydroxy-sec-butyl, and, preferably, bis(hydroxymethyl)methyl especially hydroxyethyl and 2,3-dihydroxypropyl.

When X is $-CH_2NH.Acyl$ and/or Y is $-NH.Acyl$, acyl is derived from an aliphatic carboxylic acid of 2-6 carbon atoms. Suitable ones include, in particular, aliphatic carboxylic acid residues of 2-4 carbon atoms, e.g., propionyl and, preferably, acetyl.

Preferably suitable are acyl groups substituted in the alkyl group by 1-5, preferably 1-3 hydroxy groups. One example is hydroxypropionyl; hydroxyacetyl is preferred.

Any OH-groups present in the alkyl groups $R_1$, $R_2$, $R_3$, $R_4$, $R_5$ and in the Acyl group can be etherified with a lower alkyl group of 1-3, preferably 1-2 carbon atoms, examples include methoxy and ethoxy, such as methoxyacetyl and methoxyethyl.

When the compounds of Formula I are to be utilized in the form of their physiologically compatible salts, all inorganic and organic bases well known for this purpose to those skilled in the art are suitable. The salts are conventionally produced by reacting the corresponding acid with the base in a manner known per se.

Physiologically compatible salts with bases include metallic salts, e.g., sodium, lithium, calcium, and magnesium salts, as well as amine salts, e.g., glucamine, N-methylglucamine, N,N-dimethylglucamine, ethanolamine, diethanolamine, morpholine salts and others. Also suitable are salts of basic amino acids, e.g., lysine, ornithine, arginine salts or similar compounds.

The present invention encompasses ionic X-ray contrast media based on these opacifying compounds having novel basic structures. These opacifying compounds of this invention are distinguished by a number of advantages.

They are derived from triiodinated aromatics as the basic component. These, themselves, are hydrophilic and relatively nontoxic. Thereby, the introduction of relatively heavy hydrophilic substituents to reduce chemotoxicity can be omitted, whereby the compounds of this invention have a high iodine content. In several representatives of this class of compounds this content is even above that of diatrizoic acid and iothalamic acid.

In contradistinction to the X-ray contrast media derived from triiododiaminobenzoic acid and triiodoaminoisophthalic acid, the compounds of this invention do not exhibit an amino group impairing neural compatibility. The substitution of the aromatic amino group by hydrophilic carbon substituents considerably increases the general compatibility of the compounds of this invention.

Table I presents a comparison of the conventional contrast media iothalamic acid (E) and diatrizoic acid (F) with 5-Carbamoyl-3-N-methylcarbamoyl-2,4,6-triiodobenzoic acid (D) of this invention, in terms of neural compatibility after intracerebral or intracisternal administration, as well as their general compatibility.

The compounds are administered, as meglumine salts dissolved in water, to 10 rats each in varying doses. After intracerebral and intracisternal injection, the animals are observed for 24 hours; the $ED_{50}$ is denoted as the dose causing toxic effects (strong behavioral anomalies and disturbances in motor coordination, convulsions, or death) in 50% of the animals. After intravenous injection, the observation time was 7 days. $ED_{50}$ and $LD_{50}$ were calculated by probit analysis.

TABLE I

| | Neural and General Compatibility of Derivatives of Triiodotrimesic Acid (shown for Compound C) As Compared with Iothalamic Acid (E) and Diatrizoic Acid (F) | | | | |
|---|---|---|---|---|---|
| | Iodine Content of Acid [%] | Administration Intracerebrally, Rat | | Intracisternally, Rat | | Intravenously Rat, $LD_{50}$ g I/kg |
| Compound | | $ED_{50}$ mg I/kg | $LD_{50}$ mg I/kg | $ED_{50}$ mg I/kg | $LD_{50}$ mg I/kg | |
| D | 63.5 | 42 | 66 | 13.2 | 65 | 8.7 |
| E | 62.1 | 36 | 52 | 10.6 | 58 | 7.4 |
| F | 62.1 | 12 | | 3.0 | | 7.3 |

Because of their good compatibility, the compounds of this invention are suitable for all applications wherein iodine-containing, renally excretable contrast media are utilized. Because of their good general compatibility, use is especially advantageous, e.g., via intravenous injection, e.g., in urography and in computer tomography. Additionally, their desirable osmodiuretic activity is of advantage in urography to fill the excretory urinary tract.

The present invention consequently also relates to novel X-ray contrast media based on the compounds of Formula I, e.g., for administration to mammals, including humans.

The preparation of the novel X-ray contrast media based on the compounds of this invention takes place conventionally, for example by placing the opacifying compound together with the additives customary in galenic pharmacy, for example stabilizers, such as sodium edetate, calcium disodium edetate, physiologically compatible buffers, sodium chloride, and similar compounds, into a form suitable, e.g., for intravenous or other administration. The concentration of the novel X-ray contrast media in the aqueous medium is dependent on the method used in X-ray diagnostics and can be determined by fully conventional considerations, e.g., in conjunction with standard pharamacological protocols. The preferred concentrations and dosages of the novel compounds of this invention range from 50 to 400 mg I/ml for the concentration, and 5 to 500 ml for the dosages. Especially preferred are concentrations of 100 to 400 mg I/ml. Administration can be effected analogously to the aforementioned conventional agents.

The present invention relates furthermore to a process for preparing the compounds of this invention, comprising, conventionally, (a) reacting a compound of Formula A

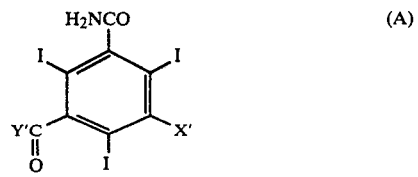

wherein
X' is —CONR$_1$'R$_2$', —CH$_2$OH, or —CH$_2$NH.Acyl,
Y' is —NR$_3$'R$_4$', —NH.Acyl, or —OR$_5$, and
R$_1$', R$_2$', R$_3$', R$_4$', and R$_5$ are as defined above for R$_1$,R$_2$,R$_3$,R$_4$, and R$_5$, but wherein R$_1$' and R$_2$' as well as R$_3$' and R$_4$' are not simultaneously hydrogen, and
Acyl is as defined above, with a diazotizing reagent; or (b) hydrolyzing the carboxylic acid halogenide group in a compound of Formula B

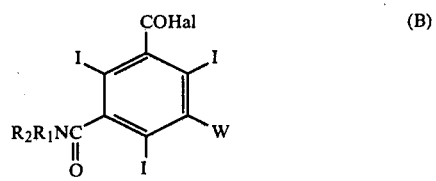

wherein
W is —CONR$_3$R$_4$, —CONH.Acyl, —CH$_2$OH, or —CH$_2$NH.Acyl, Hal is bromine or chlorine, and
R$_1$, R$_2$, R$_3$, R$_4$, and Acyl are as defined above, or
(c) reacting a compound of Formula C

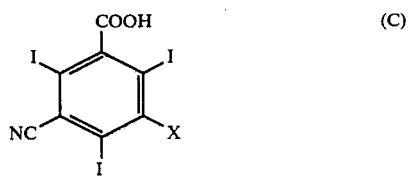

wherein X is as defined above, with a reactive derivative of an aliphatic carboxylic acid Acyl.OH, wherein Acyl is as defined above, or subjecting it to partial hydrolysis, and, optionally diazotizing the thus-obtained 5-carbamoyl compound, wherein R$_1$ and R$_2$ are not simultaneously hydrogen, and, subsequently partially amidating it, and hydrolyzing the thus-produced monocarboxylic acid chloride and, if desired, subsequently, N-alkylating the thus-obtained compounds of Formula I and/or splitting off blocking groups and/or preparing salts by reaction with inorganic or organic bases.

The conversion of a primary amide group into the carboxylic acid according to process (a) can be effected by methods known to persons skilled in the art. For example, carboxylic acid amides can be hydrolyzed by heating in aqueous mineral acids or in aqueous alkali hydroxide solutions. The method preferred in the process of this invention, however, is the "diazotization" of the primary amide group with diazotizing reagents such as, for example, nitrous acid, in an aqueous medium, or with nitrosyl sulfate or nitrosyl chloride in an anhydrous medium, wherein the carboxylic acid is obtained with nitrogen being split off. For the practical conduction of the process, a suspension of the starting material in a dilute mineral acid, e.g., sulfuric acid, preferably hydrochloric acid, is combined with a solution of the diazotizing reagent, such as, for example, the aqueous solution of sodium nitrite, or the solution or suspension of the starting material is combined in glacial acetic acid, concentrated sulfuric acid, dimethylformamide, or similar compounds, with the nitrosyl sulfate solution prepared from sodium nitrite and concentrated sulfuric acid, or with nitrosyl chloride at 0° C. to 5° C. and, after completion of diazotization, mixed with water. Subsequently, the reaction solution is suitably heated for a period of time sufficient to split off nitrogen.

In order to prepare compounds of Formula I containing an ester group —$COOR_5$ in the 5-position, the starting compound employed is suitably the free carboxylic acid, which is esterified according to methods known to those skilled in the art. If the alkyl residue $R_5$ contains one or more hydroxy groups, $R_5$ is suitably used as the halogenide $R_5$Hal by reacting the latter in a suitable solvent, preferably dimethylformamide or dimethylacetamide, with the alkali salt of the acid, preferably the sodium salt.

In addition to this esterification method, preferred within the scope of the present invention, the esterification of the carboxy group can also be effected according to other methods conventional for this purpose, especially if the $R_5$ residue to be introduced does not contain any additional hydroxy groups. Worth mentioning as an example is the esterification with dialkyl sulfate or diazoalkanes and similar compounds, or the reaction of the carboxy group with an alcohol $R_5$OH, preferably in the presence of, for example, a mineral acid such as sulfuric acid. The esterification of the carboxy group by the above-described methods can take place in the presence of other nuclear-positioned groups, such as the cyano, carbamoyl, hydroxymethyl, amidoacyl, methylaminoacyl groups etc., in addition to another carboxy group.

If, during the course of the process of this invention [process version (b)], the carboxylic acid halogenide group is hydrolyzed to the free carboxylic acid, this reaction likewise takes place according to conventional methods. For example, the carboxylic acid halogenides can be hydrolyzed to the carboxylic acids in an aqueous medium, suitably in the presence of a solubilizer such as dioxane, acetone, tetrahydrofuran, preferably dimethyl sulfoxide, and in the presence of tertiary bases, such as triethylamine, pyridine, or in the presence of alkali hydroxide, at a temperature of about room temperature to 100° C.

The conversion of the cyano group [process version (c)] into the N-acylated amide group —CONH.Acyl (Acyl being as defined above) is accomplished by chemical addition of an aliphatic carboxylic acid Acyl-OH to the CN-triple bond by means of operating methods known for this purpose to persons skilled in the art. For conductance of the reaction under practical conditions, the acid Acyl—OH is suitably utilized in the form of a reactive derivative, preferably as the anhydride. The reaction takes place in the presence of a suitable acidic catalyst, such as, for example, perchloric acid or sulfuric acid, phosphoric acid, and similar compounds. Normally, the acid anhydride employed also serves simultaneously as the solvent, which does not exclude the possibility of adding to the reaction mixture a suitable solubilizer, e.g., dioxane. The reaction takes place at room temperature or at an elevated temperature. If the reaction takes place at an elevated temperature, the preferred temperature range is 40°–110° C.

The partial hydrolysis of the nitrile group to the primary amide, necessary during the course of the process, is also effected according to processes known to persons skilled in the art. Thus, the nitrile group can be converted into the amide, for example, by dissolving the starting compound in concentrated mineral acids, such as hydrochloric acid, sulfuric acid, or phosphoric acid, and conducting the hydrolysis at temperatures of about room temperature to 100° C. The nitrile group can, however, also be partially hydrolyzed in an alkaline medium by dissolving or suspending the starting compound in aqueous alkali hydroxide and hydrolyzing at a temperature of about room temperature to 100° C., preferably at 40°–80° C.

The optionally following diazotization according to process version (c) takes place conventionally as described in connection with process version (a).

The partial amidation is effected by following conventional methods, reacting the dicarboxylic acid to the dicarboxylic acid chloride, optionally with intermediate protection of any free hydroxy groups present, if desired in a suitable solvent such as, for example, benzene, toluene, or acetonitrile, with a chlorinating reagent, such as phosphorus pentachloride, oxalyl chloride, phosgene, or 1,1-dichloromethylmethyl ether, preferably chloride, at a temperature from room temperature to 100° C., preferably 50°–80° C.; concentrating under vacuum after the hydrogen chloride liberation has ceased; and isolating the dicarboxylic acid dichloride in the usual way. The partial reaction of the dichloride with the base HN($R_1R_2$) is likewise accomplished according to conventional methods, for example by combining the dicarboxylic acid dichloride, dissolved or suspended in a suitable solvent, e.g., toluene, dioxane, preferably dimethylacetamide, in the presence of one mole of a tertiary base, e.g., tributylamine, triethylamine, or pyridine, with a solution of one mole of base HN$R_1R_2$ (10% excess) in the same solvent; allowing the mixture to react at a temperature of 10°–100° C., preferably 50°–90° C.; and subsequently isolating the monoamide monochloride in the usual way.

The subsequent N-alkylation is executed after intermediate protection of the hydroxy groups, for example, by first treating the corresponding acid amide with a proton acceptor, such as sodium amide, sodium hydride, or also an alkali hydroxide, and then reacting with an $R_5$-alkyl halogenide, preferably as the bromide, or especially with a dialkyl sulfate (e.g., dimethyl or diethyl sulfate). Depending on the proton acceptor employed, the reaction takes place in an anhydrous or aqueous reaction medium at a reaction temperature of about room temperature to 100° C., preferably 50°–70° C. Suitable solvents or solubilizers include, as is known, acetone, dimethylformamide, dioxane, tetrahydrofuran, and similar agents.

The intermediate protection of free hydroxy groups takes place according to conventional methods by means of blocking groups which can be readily split off again. The introduction of such groups can be obtained by acylation (e.g., introduction preferably of an acetyl residue or benzoyl residue), by etherification (e.g., introduction of the triphenylmethyl residue), or by acetalization or ketalization, e.g., by means of acetaldehyde, dihydropyran, acetone, or 2,2-dimethoxypropane.

The subsequent splitting off of the intermediarily introduced blocking groups, with liberation of the finally desired hydroxy groups, likewise takes place by means of methods known to those skilled in the art. Thus, the blocking groups can be split off without a separate reaction stage during the working up and isolation of the reaction products. However, it is also possible to effect this splitting-off step in the usual way in a separate reaction stage. Acetal, ketal, or ether blocking groups can be split off, for example, by acidic hydrolysis.

The reaction of the acids of this invention of Formula I to the physiologically compatible salts using the inorganic or organic bases known for this purpose to those skilled in the art likewise can take place by following conventional methods.

The starting compounds used according to the process can be prepared by conventional methods, for example from the known compounds of the formula

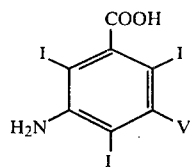

wherein V is —NH₂, —COOH, —CH₂NH.Acyl, or —CH₂OH.

In this procedure, in a Sandmeyer reaction, the aromatic amino group is substituted by the cyano group, as is explained in greater detail below, using as examples the preparation of 3,5-dicyano-2,4,6-triiodobenzoic acid and 5-cyano-2,4,6-triiodoisophthalic acid;

3,5-DICYANO-2,4,6-TRIIODOBENZOIC ACID 7 g of sodium nitrite is introduced under stirring into 84 ml of concentrated sulfuric acid held at a temperature of +5° C. The mixture is then maintained at +70° C. until solution has occurred, and then cooled to +5° C. After adding 42 ml of glacial acetic acid dropwise under cooling, 21 g of 3,5-diamino-2,4,6-triiodobenzoic acid is added in incremental portions under agitation in such a way that the internal temperature ranges between 0° C. and +5° C. The batch is stirred for another 2 hours, and the green-colored suspension is poured on 400 g of ice. A mixture is prepared from 500 ml of concentrated ammonia and 320 ml water, and 35.6 g of copper(I) cyanide and 67 g of potassium cyanide are dissolved therein. To this solution, the diazotizing batch is added under strong frothing. The mixture is stirred for 2 hours, and after allowing the batch to stand overnight it is first combined with 500 ml of ethyl acetate, then with excess concentrated hydrochloric acid. After the thus-separated copper salts have been removed by vacuum-filtering and washed out with ethyl acetate, the aqueous phase in the filtrate is separated and extracted several times with ethyl acetate. The ethyl acetate extracts are combined, washed with water, and then dried over sodium sulfate and concentrated. The dark-colored residue is treated with 100 ml of acetone in the hot state; the acetonic solution is filtered off from undissolved components and thereafter concentrated to half the quantity. After stirring for several hours, the crystallized product is vacuum-filtered, washed with ice-cold acetone, and dried at 50° C., thus obtaining 8.5 g (=38% of theory) of 3,5-dicyano-2,4,6-triiodobenzoic acid as a white powder with a decomposition point lying above 280° C.

5-CYANO-2,4,6-TRIIODOISOPHTHALIC ACID 112 g of 5-amino-2,4,6-triiodoisophthalic acid is suspended in 1100 ml of water and made to dissolve by adding 10 g of caustic soda. The solution is then cooled, after having been adjusted to pH 2.5 by adding dilute sulfuric acid, to 0° C., and under cooling a solution of 20 g of sodium nitrite in 60 ml of water is added dropwise, while maintaining the reaction temperature at 0°–5° C. The pH value is then again adjusted to 2.5 by the dropwise addition of dilute sulfuric acid, and the mixture is stirred under ice cooling for 1–2 hours. By gradually adding dilute sodium hydroxide dropwise, the produced precipitate is made to dissolve at pH 4.5.

In the meantime, a solution of 99 g of copper(I) chloride and 172 g of potassium cyanide in 800 ml of water, warmed to 30° C., is prepared, and the neutralized diazonium salt solution is added all at once, causing strong frothing. The mixture is allowed to stand for 15 minutes at 30° C. and then the copper salts are separated by acidifying the reaction solution to pH 3 with dilute sulfuric acid. The filtrate is brought to pH 0.5–1 by adding more dilute sulfuric acid, and the precipitate is vacuum filtered after agitation for several hours in an ice bath, washed with water, and dried at 50° C. For purifying purposes, the crude product is suspended in 400 ml of water, dissolved by adding sodium hydroxide solution, the solution treated with 10 g of active carbon, allowed to stand under agitation at room temperature for 30 minutes, and the filtrate combined with an excess of a mineral acid. After several hours of agitation in an ice bath, the precipitate is vacuumfiltered, washed with water, and dried at 50° C., thus obtaining 89 g (78% of theory) of 5-cyano-2,4,6-triiodoisophthalic acid as a white powder having a decomposition point of above 300° C.

Analogously the following compounds are produced from the corresponding amino compounds:

5-cyano-3-N,N-dimethylcarbamoyl-2,4,6-triiodobenzoic acid; mp 240° C. (decomposition); yield: 85% of theory;

5-cyano-3-(N-methylcarbamoyl)-2,4,6-triiodobenzoic acid; mp 300° C. (decomposition); yield: 72% of theory;

5-cyano-3-[N-methyl-N-(2-hydroxyethyl)carbamoyl]-2,4,6-triiodobenzoic acid; mp 280° C. (decomposition); yield: 89% of theory;

5-cyano-3-carbamoyl-2,4,6-triiodobenzoic acid; mp >300° C. (decomposition); yield: 82% of theory;

5-cyano-3-[N-(2-hydroxyethyl)carbamoyl]-2,4,6-triiodobenzoic acid; mp >300° C. (decomposition); yield: 95% of theory;

5-cyano-3-acetylaminomethyl-2,4,6-triiodobenzoic acid; mp 271° C. (decomposition); yield: 85% of theory;

5-cyano-3-hydroxymethyl-2,4,6-triiodobenzoic acid; mp 250°–252° C. (decomposition); yield: 81% of theory.

As indicated above, the esterification of the carboxy group takes place according to methods known per se; in this connection, methods as described for the esterification of triiodinated aminobenzoic acid derivatives are preferred. The esterification will be explained in the following preparation schemes:

5-CYANO-3-N-METHYLCARBAMOYL-2,4,6-TRIIODOBENZOIC ACID (2,3-DIHYDROXYPROPYL) ESTER 60 g of 5-cyano-3-N-methylcarbamoyl-2,4,6-triiodobenzoic acid is heated in 150 ml of dimethylformamide with 22 g of sodium carbonate (anhydrous) and 28 g of 1-chloro-2,3-propanediol for 4 hours to 90° C. Thereafter the mixture is cooled, vacuum-filtered from the precipitated sodium chloride, and concentrated to dryness under vacuum. The residue is dissolved in 250 ml of ethyl acetate, the solution is filtered over active carbon, and the filtrate is concentrated to half its quantity. The product is cooled in an ice bath and gently combined with such an amount of diisopropyl ether that crystallization sets in. After agitating for several hours in an ice bath, the crystallized product is vacuum-filtered, washed with diisopropyl ether, and dried at 50° C., thus obtaining 48.5 g (=74% of theory) of 5-cyano-3-N-methylcarbamoyl-2,4,6-triiodobenzoic acid (2,3-dihydroxypropyl) ester as a white powder, mp 117°–120° C.

5-CARBAMOYL-3-N-METHYLCARBAMOYL-2,4,6-TRIIODOBENZOIC ACID (2,3-DIHYDROXYPROPYL) ESTER 24 g of 5-carbamoyl-3-N-methylcarbamoyl-2,4,6-triiodobenzoic acid is suspended in 200 ml of water and dissolved by adding concentrated sodium hydroxide solution at pH 7. The mixture is concentrated to dryness under vacuum, and the sodium salt is dissolved in 60 ml of dimethylformamide. Then 10 g of 1-chloro-2,3-propanediol is added, and the mixture is stirred for 6 hours at 90° C. After cooling to room temperature, the precipitated sodium chloride is vacuum-filtered, and the filtrate dried out under vacuum. The residue is stirred with 40 ml of water for 2 hours. The precipitate is vacuum-filtered, washed with water, and dried at 50° C., thus obtaining 23.5 g (=87% of theory) of 5-carbamoyl-3-N-methylcarbamoyl-2,4,6-triiodobenzoic acid (2,3-dihydroxypropyl) ester, mp 258° C. (decomposition).

If cyano precursors are utilized in the preparation of the starting compounds [process version (c)], the cyano group is conventionally saponified as described above in an acidic or alkaline medium to obtain the primary amide. This reaction will be described in greater detail, using as example 5-cyano-2,4,6-triiodoisophthalic acid:

5-CARBAMOYL-2,4,6-TRIIODOISOPHTHALIC ACID 100 g of 5-cyano-2,4,6-triiodoisophthalic acid is suspended in 400 ml of water and dissolved by adding 20 g of sodium hydroxide. The solution is maintained at +60° C. for 3 hours, then poured under stirring into 60 ml of concentrated hydrochloric acid. After several hours of agitation in an ice bath the precipitated product is vacuum-filtered, washed with a small amount of ice-cold water, and dried at 50° C., thus obtaining 98 g of 5-carbamoyl-2,4,6-triiodoisophthalic acid as a white powder having a decomposition point of above 280° C.

The same compound is also obtained by acidic saponification of the nitrile group in the following process:

100 g of 5-cyano-2,4,6-triiodoisophthalic acid is suspended in 400 ml of concentrated sulfuric acid and heated first under agitation for 30 minutes to 60° C., then for 2 hours to 95° C. The thus-produced, clear solution is then poured on 1.2 kg of ice and stirred for one hour in an ice bath. The thus-precipitated crude product is vacuum-filtered, dissolved under heating in 400 ml of ethanol, and the solution is combined with 70 ml of concentrated sodium hydroxide solution. After several hours of agitation in an ice bath, the thus-separated sodium salt is vacuum-filtered, washed with ethanol, and then dissolved in 200 ml of hot water. After treating the solution with active carbon, the filtrate is precipitated into 150 ml of semiconcentrated sulfuric acid. After several hours of stirring in an ice bath, the precipitate is vacuum-filtered, washed with a small amount of ice-cold water, and dried at 50° C., thus obtaining 84 g (=82% of theory) of 5-carbamoyl-2,4,6-triiodoisophthalic acid, which conforms in its properties with the product of the alkaline saponification.

The following compounds are prepared analogously from the corresponding cyano precursors:

5-carbamoyl-2,4,6-triiodoisophthalic acid bis(N-methylamide); mp >300° C.; yield: 82% of theory;

5-carbamoyl-2,4,6-triiodoisophthalic acid bis[N-(2,3-dihydroxypropyl)amide], mp >300° C. (decomposition); yield: 70% of theory;

3-[N-(2-hydroxyethyl)carbamoyl]-5-N-methylcarbamoyl-2,4,6-triiodobenzoic acid amide; mp 300° C.; yield: 75% of theory;

3,5-bis[N-(2-hydroxyethyl)carbamoyl]-2,4,6-triiodobenzoic acid amide; mp 300° C. (decomposition); yield: 75% of theory;

3-[N-(2,3-dihydroxypropyl)carbamoyl]-5-[N-methyl-N-(2,3-dihydroxypropyl)carbamoyl]-2,4,6-triiodobenzoic acid amide; mp 202° C.; yield: 61% of theory;

5-carbamoyl-2,4,6-triiodoisophthalic acid bis[N-(2-hydroxyethyl)amide]; mp 300° C.; yield: 75% of theory;

5-carbamoyl-2,4,6-triiodoisophthalic acid bis[N-methyl-N-(2,3-dihydroxypropyl)amide]; mp >193° C.; yield: 50% of theory;

5-carbamoyl-2,4,6-triiodoisophthalic acid bis[N,N-(2-hydroxyethyl)amide]; mp 198°–200° C.; yield: 69% of theory;

5-carbamoyl-2,4,6-triiodoisophthalic acid bis[N-(trishydroxymethyl)methylamide]; mp >280° C.; yield: 67% of theory.

The preparation of the dicarboxylic acid dichlorides required for the amidation reaction and of the monocarboxylic acid chlorides required as the starting compounds, from the corresponding carboxylic acid precursors, takes place according to methods known to a person skilled in the art, as they have been described above and will be explained with reference to the following manufacturing process:

5-CARBAMOYL-2,4,6-TRIIODOISOPHTHALIC ACID DICHLORIDE 59.9 g of 5-carbamoyl-2,4,6-triiodoisophthalic acid is stirred under reflux with 500 ml of thionyl chloride and 0.5 ml of dimethylformamide for 4 hours. The reaction mixture is then concentrated under vacuum, and the residue stirred for one hour with 300 ml of methylene chloride. The crude product is then filtered off and dried under vacuum at 50° C. The product is thereafter stirred for one hour with 85 ml of acetone, vacuum-filtered, and dried at 50° C. under vacuum. Result: 36.6 g of 5-carbamoyl-2,4,6-triiodoisophthalic acid dichloride having a decomposition point of 247°-248° C.; yield: 58% of theory.

Analogously, the following compounds are prepared from the corresponding carboxylic acid precursors:
5-N-methylcarbamoyl-2,4,6-triiodoisophthalic acid dichloride; mp 214°-216° C.; yield: 48% of theory;
5-N,N-dimethylcarbamoyl-2,4,6-triiodoisophthalic acid dichloride; mp 272°-273° C.; yield: 85% of theory;
5-cyano-2,4,6-triiodoisophthalic acid dichloride; mp 246°-264° C.; yield: 94% of theory;
5-[N-(2-acetoxyethyl)carbamoyl]-2,4,6-triiodoisophthalic acid dichloride; mp 75°-85° C.; yield: 93% of theory.

5-CYANO-3-N-METHYLCARBAMOYL-2,4,6-TRIIODOBENZOYL CHLORIDE 58.2 g of 5-cyano-3-N-methylcarbamoyl-2,4,6-triiodobenzoic acid is heated under agitation to boiling for one hour in 400 ml of thionyl chloride with the addition of 0.3 ml of dimethylformamide. Thereafter the mixture is filtered and evaporated to dryness under vacuum. The residue forms a solid foam. For purification, the product is dissolved in 625 ml of dioxane by heating on a steam bath, treated on the steam bath with 6.3 g of carbon for 10 minutes, filtered, concentrated to about one-fifth, and cooled. The precipitate is vacuum-filtered and dried under vacuum at 50° C. over KOH pellets. Yield: 33.8 g (56.3% of theory) of 5-cyano-3-N-methylcarbamoyl-2,4,6-triiodobenzoyl chloride, mp 265°-267° C.

The amidation of the two acid chloride groups in the 1- and 3-positions can take place in one reaction step, thus forming bisamides, or it can also be conducted in stages, according to methods known to those skilled in the art. If the two 1- and 3-positioned amide residues in the finally desired reaction product are the same regarding the N-substituents ($R_1=R_3$ and $R_2=R_4$) then amidation is preferably carried out in one reaction step. However, if these two amide groups differ with respect to the N-substituents $R_1$ through $R_4$, then the amidation takes place preferably in stages. The monoamides-monochlorides obtained in the stepwise amidation are starting compounds for process version (b); however, they can also be reacted with the base $HNR_3R_4$ to desired bisamides with $-CONR_1R_2 \neq -CONR_3R_4$.

In this process, the monoamide-monochloride obtained in the first stage after reacting the dicarboxylic acid dichloride with the organic primary or secondary base $HN(R_1R_2)$ is suitably isolated by a conventional process to avoid undesirable secondary reactions, and is thereafter reacted, if desired, with the organic primary or secondary base $HN(R_3R_4)$. For the preparation of starting compounds wherein the amide groups to be introduced are identical, the dissolved dicarboxylic acid dichloride is reacted with 4 equivalents of the organic secondary or primary base $NH(R_1R_2)$ or with 2 equivalents of this base and in the presence of 2 equivalents of a tertiary base, e.g. pyridine, triethylamine, preferably tributylamine.

The following examples are to explain the amidation in one reaction step:

5-CARBAMOYL-2,4,6-TRIIODOISOPHTHALIC ACID BIS[1,1-BIS-(HYDROXYMETHYL)METHYLAMIDE]

11 g of 5-carbamoyl-2,4,6-triiodoisophthalic acid dichloride is dissolved in 22 ml of dimethylacetamide (DMA) and heated to +50° C.; under agitation, the solution is added within 5 minutes to a solution of 40 g of serinol (2-amino-1,3-dihydroxypropane) in 15 ml of DMA, the temperature rising to +62° C. Thereafter 10.5 ml of tributylamine is added and the mixture agitated for 4 hours at about 50° C. and overnight at room temperature. Then, 2.4 ml of concentrated hydrochloric acid is added dropwise until an acidic reaction occurs, and the solution is stirred dropwise into 270 ml of methylene chloride. After stirring for one hour, the mixture is decanted from the tacky precipitate and again extracted with 135 ml of methylene chloride for 30 minutes. The crude product (14.9 g) is dissolved in 110 ml of water and passed over a column with about 200 ml of cation exchanger IR 120. The aqueous eluate yields 12.5 g which is dissolved in 120 ml of water and passed over a column with about 200 ml of anion exchanger IRA 410. The eluate is stirred for 30 minutes with 1.2 g of carbon, filtered, concentrated under vacuum, and dried under vacuum at 50° C. Result: 8.4 g of 5-carbamoyl-2,4,6-triiodoisophthalic acid bis[1,1-bis(hydroxymethyl)methylamide]; mp 246°-252° C.; yield: 65% of theory.

5-CYANO-2,4,6-TRIIODOISOPHTHALIC ACID BIS[(2-hydroxyethyl)amide]

151.4 g of 5-cyano-2,4,6-triiodoisophthalic acid dichloride is combined as a suspension in 1.5 l of dioxane within 25 minutes with a solution of 75.5 ml of ethanolamine in 750 ml of dioxane (exothermic reaction to +45° C.). After stirring overnight, the mixture is mixed under agitation with 1.5 l of water, and the dioxane is distilled off under vacuum. After stirring for 2-4 hours, the precipitate is vacuum-filtered, washed with water, and dried at 50° C. under vacuum. Yield: 151.4 g (=92.5% of theory) of 5-cyano-2,4,6-triiodoisophthalic acid bis[(2-hydroxyethyl)amide]; mp 300° C.

The following compounds are analogously prepared:
5-cyano-2,4,6-triiodoisophthalic acid bis[(2,3-dihydroxypropyl)amide]; mp>280° C. (decomposition); yield: 80% of theory;
5-cyano-2,4,6-triiodoisophthalic acid bis[bis(2-hydroxyethyl)amide]; mp 212°-215° C.; yield: 78% of theory;
5-cyano-2,4,6-triiodoisophthalic acid bis[tris(hydroxymethyl)methyl amide]; mp>280° C.; yield: 70% of theory.

The following examples are to describe the stepwise amidation:

5-CYANO-3-[N-(2,3-DIHYDROXYPROPYL)CARBAMOYL]-2,4,6-TRIIODOBENZOYL CHLORIDE 18.1 g of 5-cyano-2,4,6-triiodoisophthalic acid dichloride is combined in 750 ml of dioxane at 80° C. with 7.1 g of 1-amino-2,3-propanediol and stirred for 2 hours.

The mixture is then separated from the precipitated hydrochloride of 1-amino-2,3-propanediol, and the filtrate is concentrated under vacuum. The residue is extracted by boiling with 800 ml of ethyl acetate. After concentration and cooling, 11.7 g (59% of theory) of 5-cyano-3-[N-(2,3-dihydroxypropyl)carbamoyl]-2,4,6-triiodobenzoyl chloride is crystallized from the extract as a white powder; mp 285°–288° C.

3-[N-(2,3-DIHYDROXYPROPYL)CARBAMOYL]-5-[N-(2,3-DIHYDROXYPROPYL)-N-METHYL-CARBAMOYL]-2,4,6-TRIIODOBENZONITRILE 6.6 g of 5-cyano-3-[N-(2,3-dihydroxypropyl)carbamoyl]-2,4,6-triiodobenzoic acid chloride is dissolved in 40 ml of dimethylacetamide and combined with 2.3 g of N-methylamino-2,3-propanediol. The mixture is stirred for one hour at room temperature and then concentrated under vacuum. The thus-obtained crude product can be used directly for nitrile saponification. To isolate the pure product the dilute aqueous solution of the crude product is treated with a cation exchange resin and an anion exchange resin, and the filtered solution is concentrated under vacuum to dryness, thus obtaining 5.9 g (81% of theory) of 3-[N-(2,3-dihydroxypropyl)carbamoyl]-5-[N-(2,3-dihydroxypropyl)-N-methylcarbamoyl]-2,4,6-triiodobenzonitrile; mp 215° C.

3-N,N-DIMETHYLCARBAMOYL-5-[N-(2,3-DIHYDROXYPROPYL)CARBAMOYL]-2,4,6-TRIIODO-BENZOYL CHLORIDE 2.78 l of dioxane is heated to 80° C. and combined in succession with 25 g of 1-amino-2,3-propanediol and 72.4 g of 5-N,N-dimethylcarbamoyl-2,4,6-triiodoisophthalic acid dichloride. The mixture is maintained for 10 minutes at 80° C., then the batch is rapidly cooled, the turbid solution is clarified by filtration over kieselguhr, and concentrated to dryness under vacuum. The residue is extracted repeatedly by boiling with respectively 300 ml of ethyl acetate, vacuum-filtered, and dried at 60° C., thus obtaining 34.5 g of 3-N,N-dimethylcarbamoyl-5-[N-(2,3-dihydroxypropyl)carbamoyl]-2,4,6-triiodobenzoyl chloride as a white powder; mp 145°–147° C. (decomposition); yield: 45% of theory.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

6.3 g of 5-cyano-3-[N-methyl-N-(2-hydroxyethyl)carbamoyl]-2,4,6-triiodobenzoic acid is agitated in a solution of 15 ml of 2 N sodium hydroxide solution and 10 ml of water for 2 hours at 60° C. The mixture is then cooled to room temperature, acidified with 3.25 ml of 12 N hydrochloric acid, vacuum-filtered after a certain period of time, and rinsed with water. Yield: 3.6 g (55.9% of theory) of 5-carbamoyl-3-[N-methyl-N-(2-hydroxyethyl)carbamoyl]-2,4,6-triiodobenzoic acid, mp 285°/286°–288° C. (decomposition).

EXAMPLE 2

13 g of 5-cyano-3-carbamoyl-2,4,6-triiodobenzoic acid is dissolved in 24.9 ml of water and 32.7 ml of 2 N NaOH. The mixture is then stirred for 3 hours at 60° C. After cooling to room temperature, the reaction mixture is diluted with 60 ml of water and acidified with 7 ml of concentrated hydrochloric acid. After 3 hours of agitation at room temperature the precipitate is vacuum-filtered, washed with a small quantity of water, and dried at 50° C. under vacuum. Yield: 12.6 g (93.9% of theory) of 3,5-biscarbamoyl-2,4,6-triiodobenzoic acid, mp > 300° C.

EXAMPLE 3

Analogously to Example 2, 3,5-dicyano-2,4,6-triiodobenzoic acid yields 3,5-biscarbamoyl-2,4,6-triiodobenzoic acid, mp > 300° C.

EXAMPLE 4

42.83 g of 5-cyano-3-[N-(2-hydroxyethyl)carbamoyl]-2,4,6-triiodobenzoic acid is dissolved in a solution of 105 ml of 2 N sodium hydroxide solution and 70 ml of water and stirred for 3 hours at 60° C. The filtered solution is acidified with 21 ml of 12 N hydrochloric acid after cooling in ice; the precipitate is vacuum-filtered after about 1.5 hours, a layer of fresh water is poured on top while the product is on the porous filter plate, the product is vacuum-filtered, and dried under vacuum at 50° C. For further purification the product (40 g) is dissolved in 160 ml of methanol with the addition of 6.9 ml of 11 N sodium hydroxide solution and stirred overnight at room temperature. The precipitated salt is vacuum-filtered after cooling in ice, dissolved in 400 ml of water, stirred with 4 g of carbon, and filtered. From the filtrate the pure acid is precipitated with 7 ml of 12 N hydrochloric acid. The pure acid is vacuum-filtered after 2 hours, extracted for 30 minutes in 200 ml of water, vacuum-filtered, and dried at 50° C. Yield: 21.9 g (49.7% of theory) of 5-carbamoyl-3-[N-(2-hydroxyethyl)carbamoyl]-2,4,6-triiodobenzoic acid, mp 297°/310°–312° C. (decomposition).

EXAMPLE 5

77.6 g of 5-cyano-3-(N-methylcarbamoyl)-2,4,6-triiodobenzoic acid is dissolved in 145 ml of water and 191 ml of 2 N sodium hydroxide solution and stirred for 3 hours at 60° C. The solution is diluted with 234 ml of water, cooled in ice, and the reaction product precipitated with 46 ml of concentrated hydrochloric acid. For purifying purposes, the product is suspended in 400 ml of $CH_3OH$ and combined with 20 ml of 7.9 N aqueous dimethylamine solution (about 40% strength). After temporary solution, the salt is precipitated. After allowing the mixture to stand under agitation for 60 hours, the salt is vacuum-filtered, washed with a small amount of $CH_3OH$, and dried under vacuum at 50° C. The salt is dissolved in 700 ml of water, stirred for 30 minutes with 7 g of carbon, vacuum-filtered, and precipitated with 15 ml of concentrated hydrochloric acid. After stirring overnight, the precipitate is vacuum-filtered, extracted with water, and dried at 50° C. under vacuum. Yield: 61.2 g (76.5% of theory) of 5-carbamoyl-3-N-methylcarbamoyl-2,4,6-triiodobenzoic acid, mp > 300° C.

EXAMPLE 6

59.6 g of 5-cyano-3-N,N-dimethylcarbamoyl-2,4,6-triiodobenzoic acid is dissolved in 120 ml of water and 140 ml of 2 N NaOH and stirred for 3 hours at 60° C. The solution is filtered over activated carbon and combined under agitation with 50 ml of concentrated hydrochloric acid. After cooling for several hours in an ice bath the precipitate is vacuum-filtered, washed with water, and dried at 50° C. Subsequently the crude product (61 g) is suspended in 300 ml of methanol and dissolved by adding 20 ml of 7.9 N aqueous dimethylamine solution (about 40% strength). After stirring for several hours in an ice bath the crystallized product is vacuum-filtered, washed with a small amount of ice-cold methanol, and dried under vacuum at 50° C. The salt is dissolved in 600 ml of water, the solution is filtered over active carbon and combined with 15 ml of concentrated hydrochloric acid. After stirring for several hours in an ice bath the precipitate is vacuum-filtered, washed with water, and dried at 50° C. under vacuum. Yield: 52.2 g (85% of theory) of 5-carbamoyl-3-N,N-dimethylcarbamoyl-2,4,6-triiodobenzoic acid, mp 255° C. (decomposition).

EXAMPLE 7

8.94 g of 5-cyano-3-acetylaminomethyl-2,4,6-triiodobenzoic acid is stirred in a solution of 22.5 ml of 2 N sodium hydroxide solution and 15 ml of water for 3 hours at 60° C. The mixture is then cooled in ice, acidified with 4.5 ml of 12 N hydrochloric acid, the precipitate is vacuum-filtered after 1.5 hours, washed, vacuum-filtered, and dried under vacuum at 50° C. Yield: 8.7 g (94.5% of theory) of 5-carbamoyl-3-acetylaminomethyl-2,4,6-triiodobenzoic acid, mp 228°-230° C. (decomposition).

EXAMPLE 8

27.8 g of 5-cyano-3-hydroxymethyl-2,4,6-triiodobenzoic acid is suspended in 120 ml of water and dissolved by adding 10 g of sodium hydroxide. The batch is held at 60° C. for 3 hours and then precipitated into 50 ml of semiconcentrated sulfuric acid. After several hours of agitation, the precipitate is vacuum-filtered, washed with water, and dried at 50° C., thus obtaining 25 g of 5-carbamoyl-3-hydroxymethyl-2,4,6-triiodobenzoic acid as a white powder with a decomposition point above 280° C. Yield: 88% of theory.

EXAMPLE 9

12.3 g of 3,5-bis(N-methylcarbamoyl)-2,4,6-triiodobenzoic acid amide is suspended in 80 ml of glacial acetic acid. Under agitation, a mixture of 1.66 g of sodium nitrite in 12 ml of concentrated sulfuric acid (prepared under ice cooling) is added in small portions at room temperature; during this step the temperature rises from 24° C. to 42° C. The mixture is then stirred for 3 hours at room temperature, 30 minutes at 50° C., and 90 minutes at 70° C. After agitating overnight at room temperature, the reaction mixture is stirred into 400 ml of water. The precipitate is vacuum-filtered after 4 hours, washed with water, and dried at 50° C. under vacuum. The crude product (11.9 g) is dissolved in 110 ml of water and 12 ml of 2 N sodium hydroxide solution, adjusted to pH 6.5 with 2 N acetic acid, and stirred for 30 minutes with 1 g of carbon. After the carbon has been removed by vacuum-filtering, the solution is precipitated with 16 ml of 2 N hydrochloric acid. After vacuum-filtering and drying at 50° C. under vacuum, 10.7 g (87% of theory) of 3,5-bis(N-methylcarbamoyl)-2,4,6-triiodobenzoic acid is obtained, mp>300° C.

EXAMPLE 10

112 g of 3,5-bis[N-(2-hydroxyethyl)carbamoyl]-2,4,6-triiodobenzoic acid amide is combined within 25 minutes in 665 ml of glacial acetic acid with a mixture of 13.8 g of sodium nitrite in 100 ml of concentrated sulfuric acid. The mixture is then stirred for 2 hours at room temperature, 30 minutes at about 50° C., and 1 hour at about 70° C. After cooling to room temperature the solution is stirred into 1.66 l of water. After agitating overnight at room temperature, the precipitate is vacuum-filtered, washed with a small amount of water, and dried at 50° C. under vacuum. Yield: 75.4 g of partially acetylated compound. This compound is suspended in 225 ml of water and saponified while adding a total of 30 ml of concentrated NaOH at pH 10-11 on a steam bath within 30 minutes. The warm solution is acidified with 35 ml of concentrated hydrochloric acid. The precipitate is vacuum-filtered after overnight agitation, washed with water, and dried at 50° C. under vacuum. Yield: 62.5 g (55.9% of theory) of 3,5-bis[N-(2-hydroxyethyl)carbamoyl]-2,4,6-triiodobenzoic acid, mp 288°-290° C.

EXAMPLE 11

A suspension of 33.6 g of 3,5-bis [N-(2-hydroxyethyl)carbamoyl]-2,4,6-triiodobenzamide in 60 ml of dimethylformamide is combined at room temperature under agitation within 5 minutes with 73 ml of a nitrosyl chloride solution in dimethylformamide (7.9 g of nitrosyl chloride); during this step, the mixture heats up slightly. After 2 days of agitation at room temperature, the yellowish suspension is combined with 350 ml of water and stirred for 30 minutes on a steam bath. The solution is extensively concentrated by means of a water jet aspirator at 60° C., the residue is diluted with 200 ml of water, combined with 7.5 ml of concentrated hydrochloric acid, and stirred for 30 minutes on a steam bath. During this step, a precipitate is obtained under slight gas evolution. After stirring overnight at room temperature, the precipitate is vacuum-filtered, washed with a small amount of water, and dried at 50° C. under vacuum. Yield: 24.5 g (72.7% of theory) of 3,5-bis[N-(2-hydroxyethyl)carbamoyl]-2,4,6-triiodobenzoic acid, mp 289°-291° C.

EXAMPLE 12

Analogously to Example 11, 32 g of 3-[N-(2-hydroxyethyl)carbamoyl]-5-N-methylcarbamoyl-2,4,6-triiodobenzoic acid amide is reacted in 60 ml of dimethylformamide with 7.9 g of nitrosyl chloride. Yield: 26.5 g (82% of theory) of 3-[N-(2-hydroxyethyl)carbamoyl]-5-N-methylcarbamoyl-2,4,6-triiodobenzoic acid; mp 271°-274° C.

EXAMPLE 13

7 g of 3-N,N-dimethylcarbamoyl-5-[N-(2,3-dihydroxypropyl)carbamoyl]-2,4,6-triiodobenzoyl chloride is dissolved in 15 ml of dimethyl sulfoxide. After adding 5 ml of 2 N sodium hydroxide solution, the batch is allowed to stand overnight at room temperature and then concentrated to dryness under vacuum. The residue is taken up in 20 ml of water, filtered over active carbon, and mixed under agitation with excess concentrated hydrochloric acid. After several hours of agitation, the thus-formed precipitate is vacuum-filtered, washed with a small amount of ice-cold water, and dried at 50° C., thus obtaining 6.2 g (90% of theory) of 3-N,N-dimethylcarbamoyl-5-N-(2,3-dihydroxypropyl)carbamoyl-2,4,6-triiodobenzoic acid as a white powder, mp 255°–258° C. (decomposition).

EXAMPLE 14

6 g of 5-cyano-3-N,N-dimethylcarbamoyl-2,4,6-triiodobenzoic acid is suspended in 30 ml of acetic anhydride. After adding 0.5 ml of 80% perchloric acid, the batch is held for 3 hours at 90°–95° C., filtered over active carbon, added dropwise under thorough cooling into 200 ml of water, and dissolved by adding sodium carbonate at pH 6. After treatment with active carbon, the solution is combined with an excess of concentrated hydrochloric acid, and the precipitate, after vacuum-filtering and washing with water, is dissolved in 40 ml of acetone. After several hours of stirring in an ice bath, the crystallized product is vacuum-filtered, washed with a small amount of ice-cold acetone, and dried at 50° C., thus obtaining 4.5 g (68% of theory) of 5-acetylaminocarbonyl-3-N,N-dimethylcarbamoyl-2,4,6-triiodobenzoic acid as a white powder with a decomposition point above 280° C.

EXAMPLE 15

Analogously to Example 11, 15 g of 5-carbamoyl-3-N-methylcarbamoyl-2,4,6-triiodobenzoic acid (2,3-dihydroxypropyl) ester is reacted in 30 ml of dimethylformamide with 4 g of nitrosyl chloride and worked up in the same way, thus obtaining 11 g (70% of theory) of 5-N-methylcarbamoyl-2,4,6-triiodoisophthalic acid mono-(2,3-dihydroxypropyl) ester, mp 232°–240° C.

EXAMPLE 16

| | |
|---|---|
| 5-Carbamoyl-2,4,6-triiodoisophthalic acid monomethylamide | 472.71 g |
| N-Methylglucamine | 153.83 g |
| Calcium disodium salt of ethylenediaminetetraacetic acid | 0.10 g |
| Double-distilled water up to a volume of 1000 ml | |

Procedure: The components are combined, made into a volume of 1000 ml with double-distilled water, and then heat-sterilized. Iodine content: 300 mg/ml.

EXAMPLE 17

198 g of 5-cyano-2,4,6-triiodoisophthalic acid mono-(2-hydroxy-1-hydroxymethylethyl)amide is suspended in 1500 ml of water and combined with 30 g of sodium hydroxide. The solution is agitated for 3 hours at 60° C., treated for 30 minutes with active carbon, filtered, and under cooling in an ice bath brought to pH 0.1 by adding concentrated hydrochloric acid. After agitating overnight under cooling, the precipitated crystallized product is vacuum-filtered, washed with a small amount of ice-cold water, and dried at 50° C., thus obtaining 167 g (82% of theory) of 2,4,6-triiodobenzenetricarboxylic acid 3-(2-hydroxy-1-hydroxymethylethyl)diamide as a white powder having a decomposition point above 280° C.

EXAMPLE 18

46.5 g of 5-cyano-2,4,6-triiodoisophthalic acid mono-(2-methoxyethyl)amide is suspended in 180 ml of water and dissolved by adding 9 g of sodium hydroxide. The solution is then heated for 3 hours to 60° C., treated for 30 minutes with active carbon, and brought to pH 0.1 after filtration by adding concentrated hydrochloric acid. After several hours of agitation in an ice bath, the precipitated product is vacuum-filtered, washed with water, and dried at 50° C. Yield: 43 g (90% of theory) of 5-carbamoyl-3-[N-(2-methoxyethyl)carbamoyl]-2,4,6-triiodobenzoic acid as a white powder, mp 286° C. (decomposition).

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of the formula

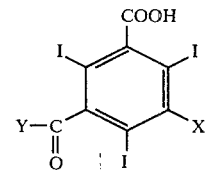

wherein
X is —CONR$_1$R$_2$, —CH$_2$NH.Acyl or —CH$_2$CH;
Y is —NR$_3$R$_4$, —NH.Acyl or OR$_5$;
R$_1$, R$_2$, R$_3$ and R$_4$ can be identical or different, and each is hydrogen, C$_{1-6}$-alkyl or C$_{2-8}$-alkyl substituted by 1–5 OH groups and/or by one C$_{1-3}$-alkoxy group;
R$_5$ is C$_{1-6}$ alkyl or C$_{2-8}$-alkyl substituted by 1–5 OH groups and/or by one C$_{1-3}$-alkoxy group;
Acyl which can be the same or different in X and Y, is C$_{2-6}$-alkanoyl or C$_{2-6}$-alkanoyl substituted by 1–4 OH groups and/or by one C$_{1-3}$-alkoxy group
or a physiologically compatible salt thereof with an inorganic or organic base.

2. 5-Carbamoyl-3-[N-methyl-N-(2-hydroxyethyl)carbamoyl]-2,4,6-triiodobenzoic acid, a compound of claim 1.

3. 5-Carbamoyl-2,4,6-triiodoisophthalamic acid, a compound of claim 1.

4. 5-Carbamoyl-3-[N-(2-hydroxyethyl)carbamoyl]-2,4,6-triiodobenzoic acid, a compound of claim 1.

5. 5-Carbamoyl-3-N-methylcarbamoyl-2,4,6-triiodobenzoic acid, a compound of claim 1.

6. 5-Carbamoyl-3-N,N-dimethylcarbamoyl-2,4,6-triiodobenzoic acid, a compound of claim 1.

7. 5-Carbamoyl-3-acetylaminomethyl-2,4,6-triiodobenzoic acid, a compound of claim 1.

8. 5-Carbamoyl-3-hydroxymethyl-2,4,6-triiodobenzoic acid, a compound of claim 1.

9. 3,5-Bis(N-methylcarbamoyl)-2,4,6-triiodobenzoic acid, a compound of claim 1.

10. 3,5-Bis[N-(2-hydroxyethyl)carbamoyl]-2,4,6-triiodobenzoic acid, a compound of claim 1.

11. 5-N-Methylcarbamoyl-3-[N-(2-hydroxyethyl)carbamoyl]-2,4,6-triiodobenzoic acid, a compound of claim 1.

12. 3-N,N-Dimethylcarbamoyl-5-[N-(2,3-dihydroxypropyl)carbamoyl]-2,4,6-triiodobenzoic acid, a compound of claim 1.

13. 5-Acetylaminocarbonyl-3-N,N-dimethylcarbamoyl-2,4,6-triiodobenzoic acid, a compound of claim 1.

14. 5-N-Methylcarbamoyl-2,4,6-triiodoisophthalic acid mono-(2,3-dihydroxypropyl) ester, a compound of claim 1.

15. 5-Carbamoyl-3-[N-(2-methoxyethyl)carbamoyl]-2,4,6-triiodobenzoic acid, a compound of claim 1.

16. A compound of claim 1, wherein $R_1$–$R_5$ are ethyl or methyl.

17. A compound of claim 1, wherein $R_1$–$R_5$ are $C_{2-4}$ alkyl substituted by 1–3 OH groups.

18. A compound of claim 1, wherein acyl is $C_{2-4}$ alkanoyl or $C_{2-4}$ alkanoyl substituted by 1–3 OH groups.

19. An X-ray contrast medium comprising an amount of a compound of claim 1 effective to make the medium opaque to X-rays after it has been administered to a host undergoing X-ray diagnosis, and a pharmaceutically acceptable carrier.

20. The X-ray contrast medium of claim 19 wherein the amount of opaque agent is 50–400 mg I/ml of medium.

21. A method of rendering an inner cavity of a host opaque to X-rays, comprising administering an X-ray contrast medium of claim 19 to the host in such a manner that it passes through the inner cavity and in such an amount that, when the medium reaches the inner cavity, it renders the cavity opaque to X-rays.

22. A method of conducting urography or computer tomography on a patient in need of the same which comprises first administering an X-ray contrast medium in accordance with claim 21 and then exposing the patient to diagnostic X-raying.

* * * * *